(12) United States Patent
Etchegaray

(10) Patent No.: US 6,867,229 B2
(45) Date of Patent: Mar. 15, 2005

(54) ANTIPARASITIC COMPOSITION FOR THE TREATMENT AND PROTECTION OF PETS

(75) Inventor: Jean Pierre Etchegaray, Toulouse (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 10/118,404

(22) Filed: Apr. 8, 2002

(65) Prior Publication Data

US 2002/0151577 A1 Oct. 17, 2002

Related U.S. Application Data

(62) Division of application No. 08/719,942, filed on Sep. 25, 1999, now Pat. No. 6,395,765.

(30) Foreign Application Priority Data

Sep. 29, 1995 (FR) .......................................... 95 11685
Sep. 11, 1996 (FR) .......................................... 96 11278

(51) Int. Cl.[7] ...................... A01N 25/02; A01N 25/22; A01N 25/30; A01N 43/56; A01N 43/40

(52) U.S. Cl. .................. 514/407; 514/156; 514/210.01; 514/211.01; 514/212.01; 514/218; 514/222.2; 514/228.8; 514/241; 514/247; 514/277; 514/359; 514/385; 514/396; 514/397; 514/399; 514/403; 514/406; 514/772; 514/772.1; 514/772.3; 514/875; 514/937; 514/946; 514/947; 514/964; 514/970; 514/971; 514/975

(58) Field of Search ................................. 514/385, 407, 514/156, 210.01, 211.01, 212.01, 218, 222.2, 228.8, 241, 247, 277, 359, 396, 397, 399, 403, 406, 772, 772.1, 772.3, 875, 937, 946, 947, 964, 970, 971, 975

(56) References Cited

U.S. PATENT DOCUMENTS

| | | | |
|---|---|---|---|
| 5,516,787 A | 5/1996 | Takada | |
| 5,849,320 A | 12/1998 | Turnblad et al. | |
| 5,876,739 A | 3/1999 | Turnblad et al. | |
| 6,010,710 A | * 1/2000 | Etchegaray | ................ 424/405 |
| 6,066,660 A | 5/2000 | Mizutani et al. | |
| 6,090,751 A | 7/2000 | Chen | |
| 6,096,329 A | * 8/2000 | Jeannin | ................ 424/405 |
| 6,265,384 B1 | 7/2001 | Pearlman | |
| 6,395,765 B1 | * 5/2002 | Etchegaray | ................ 514/407 |
| 6,413,542 B1 | * 7/2002 | Etchegaray et al. | ........ 424/438 |
| 6,482,425 B1 | * 11/2002 | Huet et al. | ................ 424/406 |
| 6,685,954 B2 | * 2/2004 | Jeannin | ................ 424/405 |

FOREIGN PATENT DOCUMENTS

| | | |
|---|---|---|
| DE | 26 33 943 | 2/1977 |
| EP | 0051786 | 5/1982 |
| EP | 0295117 | 12/1988 |
| EP | 0659745 | 6/1995 |
| FR | 2713889 | 6/1995 |
| WO | 90/09738 | 9/1990 |
| WO | 93/06089 | 4/1993 |
| WO | 96/16544 | 6/1996 |
| WO | 98/42191 | 10/1998 |
| WO | 01/30147 | 5/2001 |

OTHER PUBLICATIONS

Martindale The Extra Pharamacopoeia, 29th ed., The Pharmaceutical Press, London, pp. 1246–1247, 1437.

STN International, File CABA, STN accession no. 95:207958 J. Postal et al. "Field efficacy of a mechanical pump spray formulation XP002007096 containing 0,25% fipronil in the treatment and control of flea infestation and associated dermatological signs in dogs and cats." & Veterinary Dermatology, vol. 6, No. 3, 1995, pp. 153–158.

* cited by examiner

Primary Examiner—John Pak
(74) Attorney, Agent, or Firm—Frommer Lawrence & Haug; Thomas J. Kowalski; Judy Jarecki-Black

(57) ABSTRACT

Composition which is useful in particular for the treatment and protection of domestic animals which are infested with parasites or are likely to be infested with them, these compositions comprising, in the form of a ready-to-use solution:

a) an insecticidal active substance of formula (I),

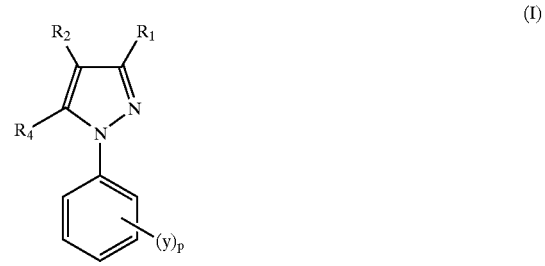

(I)

b) a crystallization inhibitor,
c) an organic solvent having a dielectric constant of between 10 and 35, preferably of between 20 and 30,
d) an organic co-solvent having a boiling point below 100° C., preferably below 80° C., and a dielectric constant of between 10 and 40, preferably of between 20 and 30.

33 Claims, No Drawings

ANTIPARASITIC COMPOSITION FOR THE TREATMENT AND PROTECTION OF PETS

This application is a divisional application of 08/719,942, filed on Sep. 25, 1999, which is now U.S. Pat. No. 6,395,765.

The present invention relates to a composition for the treatment and protection of animals which are infested with parasites or likely to be infested with them.

More particularly, the aim of the invention is to control and eliminate the parasites which infest pets, and especially cats and dogs.

Pets are often infested with one or more of the following parasites:
- cat and dog fleas (*Ctenocephalides felis, Ctenocephalides* sp. and the like),
- ticks (*Rhipicephalus* sp., *Ixodes* sp., *Dermacentor* sp., *Amblyoma* sp. and the like)
- galls (*Demodex* sp., *Sarcoptes* sp., *Otodectes* sp. and the like).

Fleas cause an animal a great deal of stress and are harmful to its health. Moreover, fleas are also vectors of pathogenic agents, such as dog tapeworm (*Dipylidium caninum*), and can also attack man.

Similarly, ticks can also cause an animal stress and be harmful to its health. They can also be harmful to man. However, the most serious problem of ticks is that they are the vector of pathogenic agents which may affect the animal as much as man. Among the major diseases which need to be avoided, mention may be made of borrelioses (Lyme disease caused by *Borrelia burgdorferi*), babesioses (or piroplasmoses caused by *Babesia* sp.) and rickettsioses (also known as Rocky Mountain spotted fever). Ticks can also release toxins with paralysing and inflammatory properties, these toxins occasionally being fatal.

Lastly, galls are particularly difficult to combat since there are very few active substances which act on these parasites, and they require frequent treatment.

Many more or less active and more or less expensive insecticides exist. However, phenomena of resistance are often associated with their use, as is the case, for example, with carbamates, organophosphorus compounds and pyrethroids.

Moreover, international patent application WO-A-87/03781 and European patent application EP-A-0,295,117 describe a large family of N-phenyl-pyrazoles with a very broad spectrum of activity, including antiparasitic activities.

The object of the invention is to provide novel antiparasitic compositions for the treatment and protection of animals, these compositions being of great efficacy while at the same time being easy to use.

Another object of the invention is to provide such compositions which are easy to use on any type of domestic animal, irrespective of its size and the nature of its coat.

Yet another object of the invention is to provide such compositions which are effective and do not need to be sprinkled over the animal's entire body.

Yet another object of the invention is to provide such compositions which, when applied locally, will subsequently diffuse over the animal's entire body and then dry, while at the same time avoiding any phenomenon of crystallization as far as possible.

Yet another object of the invention is to provide such compositions which, after drying, do not affect the appearance of the coat and in particular do not leave crystals and do not make the coat sticky.

These objects are achieved by the invention, the subject of which is antiparasitic compositions which are useful in particular in the treatment and protection of domestic animals which are infested with parasites or are likely to be infested with them, these compositions comprising, in the form of a ready-to-use solution:

a) an insecticidal active substance of formula (I),

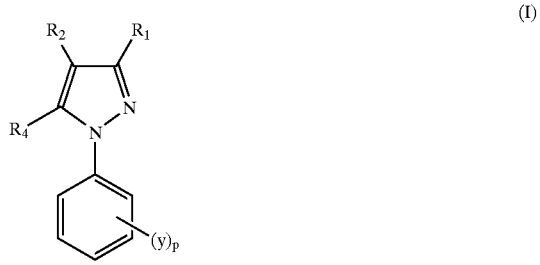

in which:

$R_1$ is a halogen atom, CN or methyl;

$R_2$ is $S(O)_nR_3$ or 4,5-dicyanoimidazol-2-yl or haloalkyl;

$R_3$ is alkyl or haloalkyl, for example lower haloalkyl;

$R_4$ represents a hydrogen or halogen atom; or a radical $NR_5R_6$, $S(O)_mR_7$, $C(O)R_7$ or $C(O)OR_7$, alkyl, haloalkyl or $OR_8$ or a radical $—N=C(R_9)(R_{10})$;

$R_5$ and $R_6$ independently represent a hydrogen atom or an alkyl, haloalkyl, C(O)alkyl, $S(O)_rCF_3$, acyl or alkoxycarbonyl radical; or $R_5$ and $R_6$ may together form a divalent alkylene radical which may be interrupted by one or two divalent hetero atoms such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or groups such as OH, —O-alkyl, —S-alkyl, cyano or alkyl;

Y represents a halogen atom or a haloalkyl or haloalkoxy radical, for example a lower haloalkoxy radical, or an $SF_5$ radical, with the possibility that:
  Y is CN or $NO_2$ in positions 2 and 6 (with reference to the carbon of the phenyl ring which is attached to the pyrazole ring and designated 1);
  the carbon in position 2 of the phenyl ring is replaced by a trivalent nitrogen atom;
  Y is $S(O)_qCF_3$ in position 4 on the phenyl ring, but preferably haloalkyl, haloalkoxy or $SF_5$;

m, n, q and r represent, independently of each other, an integer equal to 0, 1 or 2;

p is an integer equal to 1, 2, 3, 4 or 5, preferably equal to 1, 2 or 3, in particular 3;

with the proviso that when $R_1$ is methyl, then either $R_3$ is haloalkyl, $R_4$ is $NH_2$, p is 2, Y in position 6 is Cl, Y in position 4 is $CF_3$ and the carbon in position 2 of the phenyl is replaced by N; or $R_2$ is 4,5-dicyanoimidazol-2-yl, $R_4$ is Cl, p is 3, Y in position 6 is Cl, Y in position 4 is $CF_3$ and the carbon in position 2 of the phenyl is replaced by =C—Cl, it being possible for this compound of formula (I) advantageously to be present in the formulation in a proportion of from 1 to 20%, preferably from 5 to 15% (percentages expressed as weight per unit volume=W/V), b) a crystallization inhibitor which is present, in particular, in a proportion of from 1 to 20% (W/V), preferably from 5 to 15%, this inhibitor satisfying the test according to which: 0.3 ml of a solution A comprising 10% (W/V) of the compound of formula (I) in the solvent defined in c) below, and 10% of this inhibitor, are placed on a glass slide at 20° C. for 24 hours, after which few or no crystals, in particularly fewer than 10 crystals, preferably 0 crystals, are seen with the naked eye on the glass slide, c) an organic solvent having a dielectric constant of between 10 and 35, preferably of between 20 and 30, the content of this solvent c) in the overall composition preferably representing the complement to 100% of the composition, d) an organic co-solvent having a boiling point below 100° C., preferably below 80° C., and having a dielectric constant of between 10 and 40, preferably of between 20 and 30; this co-solvent may advantageously be present in the composition in a d)/c) weight/weight (W/W) ratio of between 1/15 and 1/2. The solvent is volatile so as to act in particular as a drying promoter, and is miscible with water and/or with the solvent c).

Preferably, the insecticidal active substance corresponds to formula (II),

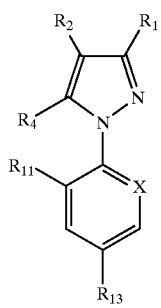

(II)

in which:
$R_1$ is a halogen atom, CN or methyl;
$R_2$ is $S(O)_n R_3$ or 4,5-dicyanoimidazol-2-yl or haloalkyl;
$R_3$ is alkyl or haloalkyl;
$R_4$ represents a hydrogen or halogen atom; or a radical $NR_5 R_6$, $S(O)_m R_7$, $C(O)R_7$ or $C(O)OR_7$, alkyl, haloalkyl or $OR_8$ or a radical $—N=C(R_9)(R_{10})$;
$R_5$ and $R_6$ independently represent a hydrogen atom or an alkyl, haloalkyl, C(O)alkyl, $S(O)_r CF_3$ or alkoxy carbonyl radical; or $R_5$ and $R_6$ may together form a divalent alkylene radical which may be interrupted by one or two divalent hetero atoms such as oxygen or sulphur;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups such as OH, —O-alkyl, —S-alkyl, cyano or alkyl;
$R_{11}$ and $R_{12}$ represent, independently of each other, a hydrogen or halogen atom and possibly CN or $NO_2$, but with H or halogen being preferred;
$R_{13}$ represents a halogen atom or a haloalkyl, haloalkoxy, $S(O)_q CF_3$ or $SF_5$ group;
m, n, q and r represent, independently of each other, an integer equal to 0, 1 or 2;
X represents a trivalent nitrogen atom or a radical C—$R_{12}$, the other three valencies of the carbon atom forming part of the aromatic ring;

with the proviso that when $R_1$ is methyl, then either $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is $=C—Cl$.

The alkyl radicals in the definition of the compounds of formulae (I) and (II) generally comprise from 1 to 6 carbon atoms. The ring formed by the divalent alkylene radical representing $R_5$ and $R_6$, along with the nitrogen atom to which $R_5$ and $R_6$ are attached, is generally a 5-, 6- or 7-membered ring.

As a further preference, $R_1$ is CN, $R_3$ is halo-alkyl, $R_4$ is $NH_2$, $R_{11}$ and $R_{12}$ are, independently of each other, a halogen atom, and $R_{13}$ is a haloalkyl. Preferably also, X is C—$R_{12}$.

A compound (A) of formula (I) which is most particularly preferred in the invention is 1-[2,6-$Cl_2$ 4-$CF_3$ phenyl] 3-CN 4-[SO—$CF_3$] 5-$NH_2$ pyrazole, whose common name is fipronil.

The compounds of formula (I) may be prepared according to one or other of the processes described in patent applications WO-A-87/3781, 93/6089 and 94/21606 or European patent application EP-A-295,117, or any other process which falls within the competence of a specialist skilled in the art of chemical synthesis. For the chemical production of the products of the invention, a person skilled in the art is considered as having at his disposal, inter alia, all of the contents of "Chemical Abstracts" and of the documents which are cited therein.

Although this is not preferred, the composition may optionally comprise water, in particular in a proportion of from 0 to 30% (volume per unit volume V/V), in particular from 0 to 5%.

The composition may also comprise an antioxidant intended to inhibit aerial oxidation, this agent being present in particular in a proportion of from 0.005 to 1% (W/V), preferably from 0.01 to 0.05%.

The compositions according to the invention intended for pets, in particular cats and dogs, are generally applied by deposition on the skin ("spot on" or "pour on" application); this is generally a localized application to a region with a surface area of less than 10 $cm^2$, especially between 5 and 10 $cm^2$, in particular at two points and preferably localized between the animal's shoulders. After deposition, the composition diffuses, in particular over the animal's entire body, and then dries, without crystallizing or changing the appearance (in particular absence of any whitish deposit or of any dusty appearance) or the feel of the coat.

The compositions according to the invention are particularly advantageous on the grounds of their efficacy, their speed of action and the pleasant appearance of the animal's hair after application and drying.

As organic solvent c) which can be used in the invention, mention may be made in particular of: acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate, or a mixture of at least two of these solvents.

The preferred solvents c) are the glycol ethers, in particular diethylene glycol monoethyl ether and dipropylene glycol monomethyl ether.

As crystallization inhibitor b) which can be used in the invention, mention may be made in particular of:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose; acrylic derivatives such as methacrylates and the like, anionic surfactants such as alkaline stearates, in particular sodium, potassium or ammonium stearate; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R''''Y^-$ in which the radicals R are hydrocarbon radicals, optionally hydroxylated, and $Y^-$ is an anion of a strong acid such as halide, sulphate and sulphonate anions; cetyltrimethylammonium bromide is among the cationic surfactants which can be used, amine salts of formula $N^+R'R''R'''$ in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as lauryl-substituted betaine compounds, or preferably a mixture of at least two of these crystallization inhibitors.

In a particularly preferred manner, use will be made of a crystallization inhibitor system, namely the combination of a film-forming agent of polymer type and a surfactant. These agents will be chosen in particular from the compounds mentioned as crystallization inhibitor b).

Among the film-forming agents of polymer type which are particularly advantageous, mention may be made of:

the various grades of polyvinylpyrrolidone, polyvinyl alcohols, and copolymers of vinyl acetate and vinylpyrrolidone.

As regards the surfactants, mention will be made most particularly of nonionic surfactants, preferably polyoxyethylenated sorbitan esters and in particular the various grades of polysorbate, for example polysorbate 80.

The film-forming agent and the surfactant may in particular be incorporated in similar or identical amounts within the limit of the total amounts of crystallization inhibitor which are mentioned elsewhere.

The system thus made up achieves, in a noteworthy manner, the aims of absence of crystallization on the hair and of maintenance of the cosmetic appearance of the coat, that is to say without a tendency to stick together or to have a sticky appearance, despite high concentration of active substance.

As co-solvent d), mention may be made in particular of: absolute ethanol, isopropanol (2-propanol), methanol.

As antioxidant, standard agents are used in particular, such as: butylated hydroxyanisole, butylated hydroxytoluene, ascorbic acid, sodium metabisulphite, propyl gallate, sodium thiosulphate, a mixture of not more than two of these antioxidants.

The compositions according to the invention are usually prepared by simply mixing the constituents as defined above; advantageously, to begin with, the active substance is mixed into the main solvent, and the other ingredients or adjuvants are subsequently added.

The subject of the present invention is also a method for the treatment and/or protection (preventive care) of animals against parasites, according to which an effective volume of a composition according to the invention is applied to a limited area of the animal, as is described above. The application is advantageously made at two points and/or on the animal's back between the shoulders.

The aim of the method may be non-therapeutic, when it concerns cleaning the animal's hair and skin by eliminating the parasites present as well as their residues and excreta. The animal thus has a coat which is pleasant to look at and to feel. This also makes it possible to prevent the establishment of fleas in the house.

The aim may also be therapeutic when it concerns treating a parasitosis which has pathogenic consequences.

The volume applied may be about 0.3 to 1 ml, preferably about 0.5 ml for cats, and about 0.3 to 3 ml for dogs, depending on the weight of the animal.

The volume of composition applied preferably corresponds to a dose of compound of formula (I) of between 0.3 and 60 mg, in particular of between 5 and 15 mg, per kg.

The examples which follow, which are given without any implied limitation, illustrate the invention and show how it may be carried out.

EXAMPLES 1 to 12

The compositions of Examples 1 to 12 are given in the following table:

|  | Example No. | | | | | | | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| Active principle (g) | 10 | 10 | 10 | 10 | 10 | 10 | 10 | 10 | 10 | 10 | 10 | 10 |
| Ethanol cm³ (g) | 10 | 7.5 | 15 | 10 | 10 | 10 | 10 | 7.5 | 15 | 10 | 10 | 10 |
| Polyvinylpyrrolidone (g) | 5 | 5 | 5 | 5 | 5 | 7.5 | 5 | 5 | 5 | 5 | 5 | 7.5 |
| polysorbate 80 (g) | 5 | 5 | 5 | 5 | 5 | 5 | 5 | 5 | 5 | 5 | 5 | 5 |
| Butylated hydroxyanisole (g) | 0.02 | 0.02 | 0.02 | 0 | 0.02 | 0 | 0.02 | 0.02 | 0.02 | 0 | 0.02 | 0 |
| Butylated-hydroxytoluene (g) | 0.01 | 0.01 | 0.01 | 0.01 | 0.01 | 0 | 0.01 | 0.01 | 0.01 | 0.01 | 0.01 | 0 |
| Diethylene glycol monoethyl ether (cm³) |  | qs | 100 cm³ |  |  |  |  |  | 0 |  |  |  |
| Dipropylene glycol monomethyl ether (cm³) |  |  | 0 |  |  |  |  |  |  | qs | 100 cm³ |  |

By way of example, the volume of diethylene glycol monoethyl ether represented by qs is about 75 cm³ for the formula of Example 1.

The following are mixed together, by stirring:
10 g of active principle 1-[4-CF₃ 2,6-Cl₂ phenyl]3-cyano 4-[CF₃—SO-]5-NH₂ pyrazole,
all of the ethanol,
60 cm³ of diethylene glycol monoethyl ether or of dipropylene glycol monomethyl ether (solvents),
all of the polyvinylpyrrolidone (Kollidon® 17PF from BASF, Germany),
all of the polysorbate 80 (Tween® from ICI),
all of the butylated hydroxyanisole (if present),
all of the butylated hydroxytoluene (if present).

The mixture is made up to 100 cm³ with diethylene glycol monoethyl ether or with dipropylene glycol monomethyl ether (for Example 1, this corresponds to a remaining volume of about 15 cm³).

Each mixture constitutes a concentrated solution S.

3 dogs, weighing about 7, 14 and 28 kg respectively, are infested with 100 fleas each. Two days later, they are treated by cutaneous application of a solution S in a proportion of 0.1 ml/kg, in localized form over about 5 cm² between the shoulders in the area of the withers. After 24 hours, the time required for complete drying, the appearance of the dogs' coat in the area of the deposition on the skin and elsewhere is identical to the initial appearance. In particular, the animal's coat is neither tacky nor sticky when touched and the coat contains no bristled tufts.

24 hours after treatment, the dogs are combed in order to remove and count any fleas which may be present. Then, at weekly intervals after the treatment, the animals are reinfested in the same way as before. 24 hours after each experimental reinfestation, the animals are again combed in order to remove and count any fleas which may still be present. Over a period of 13 weeks, it was observed that there was a percentage reduction in the population of fleas which was maintained above 95% when compared with a control group which had not received the treatment according to the invention.

EXAMPLES 12 to 24

For Examples 12 to 24, it suffices to replace, in the above table, Examples 1 to 12 by 12 to 24 respectively, with 12.5 g of active principle. The amounts of the other constituents are unchanged, apart from the amount of solvent required for the complement to 100 cm³.

The following ingredients are mixed together, by simple stirring:
12.5 g of the compound of Example 1
all of the ethanol
60 cm³ of diethylene glycol monoethyl ether or of dipropylene glycol monomethyl ether
all of the polyvinylpyrrolidone
all of the polysorbate 80
all of the butylated hydroxyanisole (if present)
all of the butylated hydroxytoluene (if present).

The mixture is made up to 100 cm³ with diethylene glycol monoethyl ether or with dipropylene glycol monomethyl ether.

When used under the conditions described in Example 1, these mixtures lead to comparable results. A greater than 95% reduction in the population of fleas is observed in less than 24 h when compared with the control group.

What is claimed is:

1. A composition for the treatment or protection of a domestic animal against parasitic infestation by topical application to a localized region and diffusion therefrom over the animal's body, the composition comprising, in the form of a ready-to-use solution:

(a) an insecticidal active substance of the formula (I)

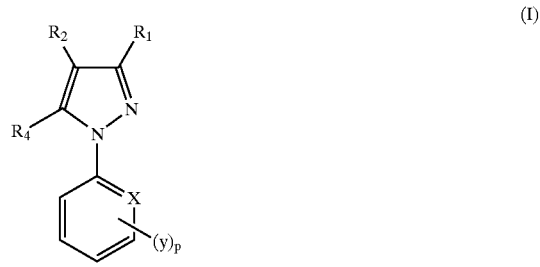

in which:
$R_1$ is a halogen atom, CN or methyl;
$R_2$ is $S(O)_n R_3$ or 4,5 dicyanoimidazol-2-yl or haloalkyl;
$R_3$ is alkyl or haloalkyl;
$R_4$ represents a hydrogen or halogen atom; $NR_5R_6$, $S(O)_m R_7$, $C(O)R_7$, $C(O)OR_7$, alkyl, haloalkyl, $OR_8$ or —N=C($R_9$)($R_{10}$);
$R_5$ and $R_6$ independently represent a hydrogen atom or an alkyl, haloalkyl, C(O)alkyl, $S(O)_r CF_3$, acyl or alkoxycarbonyl radical; or $R_5$ and $R_6$ may together form a divalent alkylene radical which may be interrupted by one or two divalent hetero atoms;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms;
X represents carbon, a trivalent nitrogen atom or a radical C—$R_{12}$;
$R_{12}$ represents a hydrogen or halogen atom, CN or $NO_2$;
Y represents $SF_5$, a hydrogen, CN, $NO_2$, $S(O)_r CF_3$, a halogen atom or a haloalkyl or haloalkoxy radical;
m, n, and r represent, independently of each other, an integer equal to 0, 1 or 2; and
p is an integer equal to 1, 2, 3, 4 or 5;
with the proviso that when $R_1$ is methyl, then either $R_3$ is haloalkyl, $R_4$ is $NH_2$, p is 2, Y in position 6 is Cl, Y in position 4 is $CF_3$ and X is N; or $R_2$ is 4,5-dicyanoimidazol-2-yl, $R_4$ is Cl, p is 3, Y in position 6 is Cl, Y in position 4 is $CF_3$ and X is C—Cl;

(b) a crystallization inhibitor selected from the group consisting of polyvinylpyrrolidone, copolymers of vinyl acetate and vinylpyrrolidone, polyoxyethylenated sorbitan esters and mixtures thereof;

(c) an organic solvent selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monomethyl ether, propylene glycol, diethylene glycol monoethyl ether, ethylene glycol, and a mixture of at least two of these solvents; and (d) an organic co-solvent selected from the group consisting of ethanol, isopropanol, and methanol;

wherein,
the compound of formula (I) is present in a proportion from 1 to 20% (W/V);

the crystallization inhibitor is present in a proportion from 1 to 20% (W/V), and meets the following test: a 0.3 mL solution comprising 10% (W/V) of the compound of formula (I) in the organic solvent defined in (c), and 10% (W/V) of said crystallization inhibitor, placed on a glass slide at 20° C. for 24 hours results in fewer than 10 crystals observed on the glass slide with the naked eye;

the organic solvent (c) is present in the overall composition in a proportion representing the compliment to 100% of the composition, with the organic co-solvent also present in a (d)/(c) weight/weight (W/W) ratio of between 1/15 and 1/2; and the organic co-solvent is miscible with water and/or solvent (c).

2. The composition according to claim 1 wherein X is carbon or the radical C—$R_{12}$, Y is CN or $NO_2$ in positions 2 and 6 of the phenyl ring.

3. The composition according to claim 1 wherein X is carbon or the radical C—$R_{12}$, wherein Y is in position 4 on the phenyl ring and is selected from the group consisting of $S(O)_r$ $CF_3$, haloalkyl, haloalkoxy and $SF_5$, wherein r represents an integer equal to 0, 1 or 2.

4. The composition according to claim 1 wherein alkyl radicals in compounds of formula (I) comprise from 1 to 6 carbon atoms.

5. The composition according to claim 1 wherein $R_5$ and $R_6$ form the divalent alkylene radical, which, along with the nitrogen atom to which $R_5$ and $R_6$ are attached, comprises a 5-, 6- or 7-membered ring.

6. The composition according to claim 1, wherein the compound of formula (I) is 1-[4-$CF_3$2,6-$Cl_2$ phenyl]3-cyano 4-[$CF_3$—SO]5-$NH_2$ pyrazole.

7. A composition for the treatment or protection of a domestic animal against parasitic infestation by topical application to a localized region and diffusion therefrom over the animal's body, the composition comprising, in the form of a ready-to-use solution:

(a) an insecticidal active substance of the formula (II):

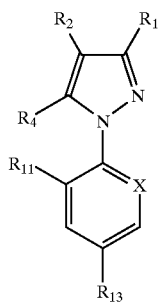

(II)

in which:

$R_1$ is a halogen atom, CN or methyl;

$R_2$ is $S(O)_n R_3$ or 4,5 dicyanoimidazol-2-yl or haloalkyl;

$R_3$ is alkyl or haloalkyl;

$R_4$ represents a hydrogen or halogen atom; $NR_5R_6$, $S(O)_m$ $R_7$, $C(O)R_7$, $C(O)OR_7$, alkyl, haloalkyl, $OR_8$ or —N=$C(R_9)(R_{10})$;

$R_5$ and $R_6$ independently represent a hydrogen atom or an alkyl, haloalkyl, C(O)alkyl, $S(O)_r CF_3$, or alkoxycarbonyl radical; or $R_5$ and $R_6$ may together form a divalent alkylene radical which may be interrupted by one or two divalent hetero atoms;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or one or more OH groups, —O-alkyl groups, —S-alkyl groups, cyano groups, or alkyl, groups;

$R_{11}$ represents a hydrogen or halogen atom, CN or $NO_2$;

$R_{13}$ represents a halogen atom or a haloalkyl, haloalkoxy, $S(O)_q CF_3$, or $SF_5$ group;

m, n, q and r represent, independently of each other, an integer equal to 0, 1 or 2;

X represents a trivalent nitrogen atom or a radical C—$R_{12}$, the other three valencies of the carbon atom forming part of the aromatic ring;

$R_{12}$ represents a hydrogen or halogen atom, CN or $NO_2$;

with the proviso that when $R_1$ is methyl, then either $R_3$ is haloalkyl, $R_4$ is $NH_2$, $R_{11}$ is Cl, $R_{13}$ is $CF_3$ and X is N; or $R_2$ is 4,5 dicyanoimidazol-2-yl, $R_4$ is Cl, $R_{11}$ is Cl, $R_{13}$ is $CF_3$ and X is C—Cl;

(b) a crystallization inhibitor selected from the group consisting of polyvinylpyrrolidone, copolymers of vinyl acetate and vinylpyrrolidone, polyoxyethylenated sorbitan esters and mixtures thereof;

(c) an organic solvent selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monomethyl ether, propylene glycol, diethylene glycol monoethyl ether, ethylene glycol, and a mixture of at least two of these solvents; and (d) an organic co-solvent selected from the group consisting of ethanol, isopropanol, and methanol:

wherein, the compound of formula (II) is present in a proportion from 1 to 20% (W/V); the crystallization inhibitor is present in a proportion from 1 to 20% (W/V), and meets the following test: a 0.3 mL solution comprising 10% (W/V) of the compound of formula (II) in the organic solvent defined in (c), and 10% (W/V) of said crystallization inhibitor, placed on a glass slide at 20° C. for 24 hours results in fewer than 10 crystals observed on the glass slide with the naked eye;

the organic solvent (c) is present in the overall composition in a proportion representing the compliment to 100% of the composition, with the organic co-solvent also present in a (d)/(c) weight/weight (W/W) ratio of between 1/15 and 1/2; and the organic co-solvent is miscible with water and/or solvent (c).

8. The composition according to claim 7 wherein X is a trivalent nitrogen atom.

9. The composition according to claim 7 wherein $R_1$ is CN, $R_3$ is haloalkyl, $R_4$ is $NH_2$, $R_{11}$ and $R_{12}$ are independently of each other a halogen atom, and $R_{13}$ is a haloalkyl.

10. The composition according to claim 7 wherein X is C—$R_{12}$.

11. The composition according to claim 7 wherein alkyl radicals in compounds of formula (II) comprise from 1 to 6 carbon atoms.

12. The composition according to claim 7 wherein $R_5$ and $R_6$ form the divalent alkylene radical, which, along with the nitrogen atom to which $R_5$ and $R_6$ are attached, comprises a 5-, 6- or 7-membered ring.

13. The composition of any one of claims 1–12, wherein the compound of part (a) is present in a proportion from 5 to 15% (W/V).

14. The composition of any one of claims 1–12, wherein the crystallization inhibitor is present in a proportion from 5 to 15% (W/V).

15. The composition of any one of claims 1–12, further comprising water present to 30% V/V.

16. The composition of claim 15, wherein the water is present to 5% V/V.

17. The composition of any one of claims 1–12, further comprising an antioxidant present in a proportion from 0.005–1% W/V.

18. The composition of claim 17, wherein the antioxidant is present in a proportion from 0.01–0.05% W/V.

19. The composition of any one of claims 1–12, wherein the crystallization inhibitor meets the following test: a 0.3 mL solution comprising 10% (W/V) of the compound of part (a) in the organic solvent defined in (c), and 10% (W/V) of said crystallization inhibitor, placed on a glass slide at 20° C. for 24 hours results in 0 crystals observed on the glass slide with the naked eye.

20. The composition according to any one of claims 1–12, wherein the polyoxyethylenated sorbitan ester is polysorbate.

21. The composition according to claim 20, wherein the is polysorbate 80.

22. The composition according to any one of claims 1–12, wherein the crystallization inhibitor comprises a mixture of polyvinylpyrrolidone and polysorbate.

23. The composition according to any one of claims 1–12, wherein the organic solvent is a glycol ether selected from the group consisting of dipropylene glycol n-butyl ether, ethylene glycol monoethyl ether, ethylene glycol monomethyl ether, diethylene glycol monoethyl ether, dipropylene glycol monomethyl ether and mixtures thereof.

24. The composition according to claim 23, wherein the glycol ether is selected from the group consisting of diethylene glycol monoethyl ether and dipropylene glycol monomethyl ether.

25. The composition according to claims 1–12, wherein the antioxidant is selected from the group consisting of butylated hydroxyanisole, butylated hydroxytoluene, ascorbic acids, sodium metabisulphite, propyl gallate, sodium thiosulfate, and a mixture of not more than two of these antioxidants.

26. The composition of any one of claims 1–12, wherein the crystallization inhibitor comprises a mixture of at least one copolymer of vinyl acetate and vinyl pyrrolidone and polysorbate.

27. A method for the treatment or the elimination of a parasitic infestation in a domestic animal which comprises topically applying to a localized region and diffusion therefrom the animal's body an effective amount of the composition according to any one of claims 1–12.

28. The method according to claim 27, wherein the animal is a cat or dog and the parasite is a flea or tick.

29. The method according to 27, wherein the animal is a cat or dog and the parasite is a tick.

30. The method according to claim 27, wherein the animal is a cat.

31. The method according to claim 27, wherein the animal is a dog.

32. A method for distributing an active agent over a domestic animal's body and thereby treating or eliminating a parasitic infestation in said animal, which method comprises topically applying to a localized region on the animal's skin an effective amount of a composition according to any one of claims 1–12.

33. The compositions according to claim 1, wherein the crystallization inhibitor is polyvinylpyrrolidone and polysorbate 80.

* * * * *